United States Patent
Yamanaka et al.

(10) Patent No.: US 9,637,732 B2
(45) Date of Patent: May 2, 2017

(54) METHOD OF EFFICIENTLY ESTABLISHING INDUCED PLURIPOTENT STEM CELLS

(75) Inventors: Shinya Yamanaka, Kyoto (JP); Kazutoshi Takahashi, Kyoto (JP); Koji Tanabe, Kyoto (JP); Hong Hyenjong, Kyoto (JP)

(73) Assignee: Kyoto University, Kyoto (JP)

( * ) Notice: Subject to any disclaimer, the term of this patent is extended or adjusted under 35 U.S.C. 154(b) by 345 days.

(21) Appl. No.: 13/824,087

(22) PCT Filed: Nov. 4, 2011

(86) PCT No.: PCT/JP2011/076017
§ 371 (c)(1),
(2), (4) Date: Apr. 4, 2013

(87) PCT Pub. No.: WO2012/060473
PCT Pub. Date: May 10, 2012

(65) Prior Publication Data
US 2013/0183757 A1    Jul. 18, 2013

Related U.S. Application Data

(60) Provisional application No. 61/410,178, filed on Nov. 4, 2010.

(51) Int. Cl.
*C12N 15/00* (2006.01)
*C12N 15/01* (2006.01)
*C12N 5/074* (2010.01)
*C12N 15/86* (2006.01)
*C12N 9/18* (2006.01)
*C12N 9/12* (2006.01)

(52) U.S. Cl.
CPC .......... *C12N 15/01* (2013.01); *C12N 5/0696* (2013.01); *C12N 9/12* (2013.01); *C12N 9/18* (2013.01); *C12N 15/86* (2013.01); *C12N 2501/405* (2013.01); *C12N 2501/60* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/999* (2013.01)

(58) Field of Classification Search
CPC ............ C12N 15/113; C12N 2310/141; C12N 5/0606; C12N 5/0696; C12N 15/63; C12N 2501/602; C12N 2501/603; C12N 2501/605; C12N 2501/727; C12N 2501/60; C12N 2501/608; C12N 2501/65; C12N 2830/003; C12N 2506/1307; C12N 2506/45; C12N 2510/00; C12N 9/12; C12N 9/18; C12N 15/86; C12N 2501/604
See application file for complete search history.

(56) References Cited

U.S. PATENT DOCUMENTS

2008/0293143 A1* 11/2008 Lin et al. .................. 435/456
2009/0068742 A1    3/2009 Yamanaka
2011/0117653 A1    5/2011 Enoki et al.

FOREIGN PATENT DOCUMENTS

| EP | 2096169 A1 | 9/2009 |
|---|---|---|
| WO | WO 01/23531 A1 | 4/2001 |
| WO | WO 2007/069666 A1 | 6/2007 |
| WO | WO 2008/124133 A1 | 10/2008 |
| WO | WO 2009/057831 A1 | 5/2009 |
| WO | WO 2009/091659 A2 | 7/2009 |
| WO | WO 2009/157201 A1 | 12/2009 |
| WO | WO 2009/157593 A1 | 12/2009 |
| WO | WO 2010/004989 A1 | 1/2010 |

OTHER PUBLICATIONS

Takahashi et al., Induction of Pluripotent Stem Cells from Adult Human Fibroblasts by DefinedFactors, Cell (2007), doi:10.1016/j.cell.2007.11.019.*
Chen et al. Cyclin D1 acts as a barrier to pluripotent reprogramming by promoting neural progenitor fate commitment. FEBS Letters, 2014, vol. 588, pp. 4008-4017.*
Mikkelsen et al. Dissecting direct reprogramming through integrative genomic analysis. Nature, 2008, vol. 454, pp. 49-56.*
Park et al. Reprogramming of human somatic cells to pluripotency with defined factors. Nature, 2008. vol. 451, pp. 141-147.*
Edel et al., *Cell Cycle*, 9(14): 2694-2695 (2010).
Edel et al., *Genes Dev.*, 24(6): 561-573 (2010).
Lee et al., *Biochem. Biophys. Res. Commun.*, 377(2): 434-440 (2008).
Lin et al., *Cancer Res.*, 70(22): 9473-9482 (2010).
Scheper et al., *Stem Cell Rev. Rep.*, 5(3): 204-223 (2009).
Okita et al., "Generation of germline-competent induced pluripotent stem cells", *Nature*, 448: 313-317 and methods information [doi:10.1038/nature05934] (Jul. 19, 2007).
Wernig et al., "In vitro reprogramming of fibroblasts into a pluripotent ES-cell-like state", *Nature*, 448: 318-324 and methods and supplementary information [doi:10.1038/nature05944] (Jul. 19, 2007).
Alt et al., *Genes & Development*, 14: 3102-3114 (2000).
Dangi-Garimella et al., *The EMBO Journal*, 28: 347-358 (2009).
Diehl et al., *Genes Development*, 11: 957-972 (1997).
Greenberg et al., *Oncogene*, 18: 1219-1226 (1999).
Guney et al., *PNAS*, 103(10): 3645-3650 (2006).
Hunter et al., *Cell*, 79: 573-582 (1994).
Russell et al., *Oncogene*, 18: 1983-1991 (1999).

* cited by examiner

*Primary Examiner* — Deborah Crouch
(74) *Attorney, Agent, or Firm* — Leydig, Voit & Mayer, Ltd.

(57) ABSTRACT

Provided is a method of improving the efficiency of iPS cell establishment, comprising bringing one or more factors selected from the group consisting of proteins belonging to cyclin D family and nucleic acids that encode the same into contact with a somatic cell, in the step of nuclear reprogramming of the somatic cell. Also provided are a method of producing an iPS cell comprising the step of bringing the factor(s) and nuclear reprogramming substance(s) into contact with a somatic cell, an iPS cell comprising a nucleic acid that encodes a protein belonging to cyclin D family that can be obtained by the method of producing an iPS cell, and a method of somatic cell production by forcing the iPS cell to differentiate.

19 Claims, 3 Drawing Sheets

METHOD OF EFFICIENTLY ESTABLISHING INDUCED PLURIPOTENT STEM CELLS

CROSS-REFERENCE TO RELATED APPLICATIONS

This patent application is the U.S. national phase of International Patent Application PCT/JP2011/076017, filed on Nov. 4, 2011, which claims the benefit of U.S. Provisional Patent Application No. 61/410,178, filed Nov. 4, 2010, which are incorporated by reference in their entireties herein.

TECHNICAL FIELD OF THE INVENTION

The present invention relates to a method of improving the efficiency of establishment of induced pluripotent stem cells (hereinafter referred to as iPS cells) and reagents therefor, more specifically to factors [genes or proteins] that improve the efficiency of establishment of iPS cells from a somatic cell and a method of improving the efficiency of establishment of iPS cells using these factors.

BACKGROUND OF THE INVENTION

In recent years, mouse and human iPS cells have been established one after another. Takahashi and Yamanaka induced iPS cells by transferring the Oct3/4, Sox2, Klf4 and c-Myc genes into fibroblasts from a reporter mouse wherein the neomycin resistance gene is knocked-in into the Fbx15 locus, and forcing the cells to express the genes [1]. Okita et al. succeeded in establishing iPS cells (Nanog iPS cells) that show almost the same gene expression and epigenetic modification profiles as those of embryonic stem (ES) cells by creating a transgenic mouse having the green fluorescent protein (GFP) and puromycin-resistance genes integrated into the locus of Nanog, whose expression is more localized in pluripotent cells than the expression of Fbx15, forcing fibroblasts from the mouse to express the above-mentioned four genes, and selecting puromycin-resistant and GFP-positive cells [2]. Thereafter, it was revealed that iPS cells could also be produced with three of the factors other than the c-Myc ogene [3].

Furthermore, Takahashi et al. succeeded in establishing iPS cells by transferring into human skin fibroblasts the same four genes as those used in the mouse [4]. On the other hand, Yu et al. produced human iPS cells using Nanog and Lin28 in place of Klf4 and c-Myc [5]. Hence, it has been demonstrated that iPS cells comparable to ES cells in terms of pluripotency can be produced in both humans and mice, by transferring defined factors into somatic cells.

However, the efficiency of iPS cell establishment is low at less than 1%. Especially, a problem of extremely low efficiency of iPS cell establishment occurs when they are produced by introducing 3 factors (Oct3/4, Sox2 and Klf4) other than c-Myc, which is feared to cause tumorigenesis in tissues or individuals differentiated from iPS cells, into somatic cells.

Recently, the present inventors have reported that the inhibition of p53-p21 pathway remarkably increases the efficiency of iPS cell establishment [6]. p53 is a tumor suppressor protein and has been described as "guardian of the genome". It has been reported that p53 is induced by cell stress and functions as a transcription factor, thereby regulating cell cycle and inducing apoptosis. However, a number of downstream genes having various biological functions have been discovered, and it has been revealed that p53 has a variety of physiological functions. Thus, it remains unsolved which factors in p53-p21 pathway are involved in reprogramming of somatic cells.

CITED REFERENCES

1. Takahashi, K. and Yamanaka, S., Cell, 126: 663-676 (2006)
2. Okita, K. et al., Nature, 448: 313-317 (2007)
3. Nakagawa, M. et al., Nat. Biotethnol., 26: 101-106 (2008)
4. Takahashi, K. et al., Cell, 131: 861-872 (2007)
5. Yu, J. et al., Science, 318: 1917-1920 (2007)
6. Hong, H. et al., Nature, 460: 1132-1135 (2009)

SUMMARY OF THE INVENTION

It is an object of the present invention to provide a means of improving the efficiency of establishment of iPS cells, and a method of efficiently producing iPS cells using the means.

The present inventors transfected mouse embryonic fibroblasts (MEFs) with various candidate genes in p53-p21 pathway, along with the 4 genes (Oct3/4, Sox2, Klf4, and c-Myc) or 3 genes (Oct3/4, Sox2 and Klf4), and examined the cells to determine whether the establishment efficiency was improved. As a result, the present inventors found that genes belonging to cyclin D family (cyclin D1, D2 and D3) remarkably improved iPS cell establishment efficiency from MEFs. These genes also improved iPS cell establishment efficiency from adult human dermal fibroblasts (HDFs). Since cyclin D genes did not have a remarkable cell proliferation-stimulating effect, it is suggested that the iPS cell establishment efficiency-improving effect of the genes is mainly due to some mechanism other than cell growth stimulation.

The present inventors conducted further investigations based on these findings, and have developed the present invention.

Accordingly, the present invention provides:

[1] a method of improving iPS cell establishment efficiency, comprising bringing one or more factors selected from the group consisting of proteins belonging to cyclin D family and nucleic acids that encode the same into contact with a somatic cell in a nuclear reprogramming step;

[2] the method according to [1] above, the proteins are cyclin D1, cyclin D2 and cyclin D3;

[3] an agent for improving iPS cell establishment efficiency comprising a factor selected from the group consisting of proteins belonging to cyclin D family and nucleic acids that encode the same;

[4] the agent according to [3] above, wherein the proteins are cyclin D1, cyclin D2 and cyclin D3;

[5] a method of producing iPS cells, comprising the step of bringing one or more factors selected from the group consisting of proteins belonging to cyclin D family and nucleic acids that encode the same, and nuclear reprogramming substance(s) into contact with a somatic cell;

[6] the method according to [5] above, wherein the nuclear reprogramming substance(s) is(are) selected from the group consisting of members of the Oct family, members of the Sbx family, members of the Klf4 family, members of the Myc family, members of Lin family and Nanog, as well as nucleic acids that encode the same;

[7] the method according to [6] above, wherein the nuclear reprogramming substances are Oct3/4, Sox2 and Klf4, or nucleic acids that encode the same;

[8] the method according to [6] above, wherein the nuclear reprogramming substances are Oct3/4, Sox2, Klf4 and c-Myc, or nucleic acids that encode the same;

[9] the method according to [6] above, wherein the nuclear reprogramming substances are Oct3/4, Sox2, Klf4 and L-Myc, or nucleic acids that encode the same;

[10] the method of any one of [5] to [9] above, wherein the proteins belonging to cyclin D family are cyclin D1, cyclin D2 and cyclin D3;

[11] an agent for inducing an iPS cell from a somatic cell, comprising a factor selected from the group consisting of proteins belonging to cyclin D family and nucleic acids that encode the same, and nuclear reprogramming substance(s);

[12] the agent according to [11] above, wherein the nuclear reprogramming substance(s) is(are) selected from the group consisting of members of the Oct family, members of the Sox family, members of the Klf4 family, members of the Myc family, members of Lin family and Nanog, as well as nucleic acids that encode the same;

[13] the agent according to [12] above, wherein the nuclear reprogramming substances are Oct3/4, Sox2 and Klf4, or nucleic acids that encode the same;

[14] the agent according to [12] above, wherein the nuclear reprogramming substances are Oct3/4, Sox2, Klf4 and c-Myc, or nucleic acids that encode the same;

[15] the agent according to [12] above, wherein the nuclear reprogramming substances are Oct3/4, Sox2, Klf4 and L-Myc, or nucleic acids that encode the same;

[16] the agent of any one of [11] to [15] above, wherein the proteins belonging to cyclin D family are cyclin D1, cyclin D2 and cyclin D3;

[17] an iPS cell containing an exogenous nucleic acid that encodes cyclin D1, cyclin D2 or cyclin D3;

[18] the iPS cell according to [17] above, wherein the exogenous nucleic acid is integrated in the genome;

[19] a method of producing a somatic cell, comprising performing a differentiation induction treatment on the iPS cell according to [17] or [18] above to cause the iPS cell to differentiate into a somatic cell;

[20] a method of producing a somatic cell, comprising the steps of:
(1) producing an iPS cell by the method according to any one of [5] to [10] above, and
(2) performing a differentiation induction treatment on the iPS cell obtained through the step (1) to cause the iPS cell to differentiate into a somatic cell;

[21] a use of one or more factors selected from the group consisting of proteins belonging to cyclin D family and nucleic acids that encode the same for improving the efficiency of establishment of iPS cells;

[22] the use according to [21] above, wherein the proteins belonging to cyclin D family are cyclin D1, cyclin D2 and cyclin D3;

[23] a use of one or more factors selected from the group consisting of proteins belonging to cyclin D family and nucleic acids that encode the same for producing an iPS cell, wherein the factor(s), along with nuclear reprogramming substance(s), is(are) brought into contact with a somatic cell;

[24] the use according to [23] above, wherein the nuclear reprogramming substance(s) is(are) selected from the group consisting of members of the Oct family, members of the Sox family, members of the Klf4 family, members of the Myc family, members of the Lin28 family, and Nanog, as well as nucleic acids that encode the same;

[25] the use according to [24] above, wherein the nuclear reprogramming substances are Oct3/4, Sox2 and Klf4, or nucleic acids that encode the same;

[26] the use according to [24] above, wherein the nuclear reprogramming substances are Oct3/4, Sox2, Klf4 and c-Myc, or nucleic acids that encode the same;

[27] the use according to [24] above, wherein the nuclear reprogramming substances are Oct3/4, Sox2, Klf4 and L-Myc, or nucleic acids that encode the same;

[28] the use according to any one of [23] to [27] above, wherein the proteins belonging to cyclin D family are cyclin D1, cyclin D2 and cyclin D3;

[29] a use of the iPS cell according to [17] or [18] above in producing a somatic cell; and

[30] the iPS cell according to [17] or [18] above as a source of cells for producing a somatic cell.

Because the iPS cell establishment efficiency improving factors of the present invention are capable of remarkably improving the efficiency of establishment of iPS cells by means of 3 factors except c-Myc, without inhibition of a master gene p53 per se, as stated above, they are useful in, for example, applying iPS cells to regenerative medicine.

DETAILED DESCRIPTION OF THE INVENTION

Figure 1:
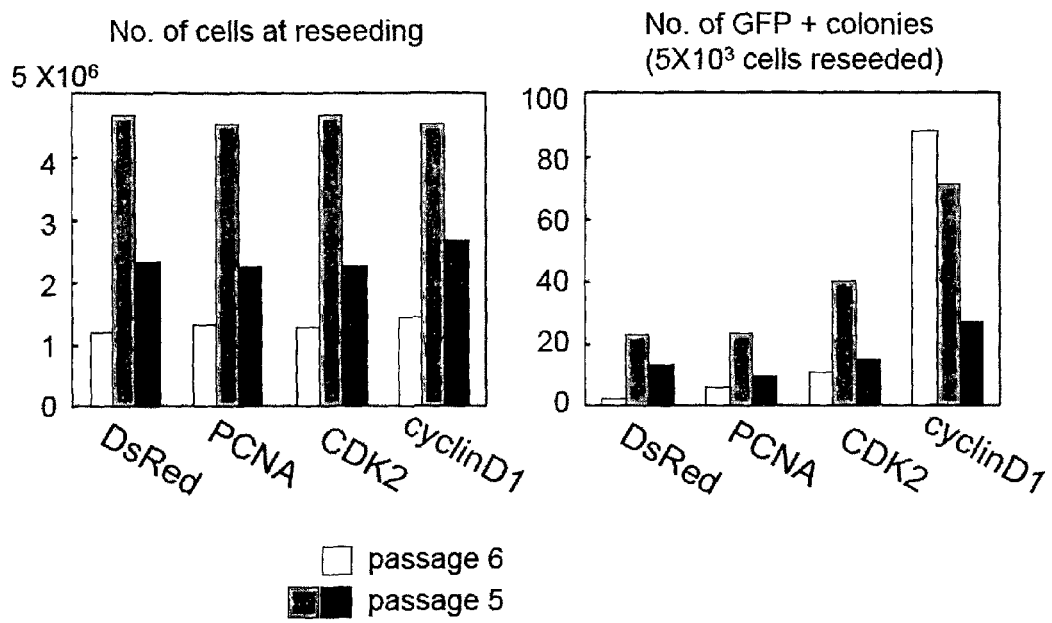
FIG. 1 shows graphs presenting the results of Example 1. The vertical axis of the left drawing shows the total number of cells, and the vertical axis of the right drawing shows the number of GFP positive colonies (iPS colony number). The horizontal axes show combinations of Oct3/4, Sox2, Klf4 and c-Myc genes and respective genes shown in the horizontal axes. The white bar shows the results of MEF at passage 6, and the gray and black bars show the results of MEF at passage 5.

The present invention provides a method of improving the efficiency of iPS cell establishment by bringing one or more factors selected from the group consisting of proteins belonging to cyclin D family and nucleic acids that encode the same (hereinafter also referred to as the establishment efficiency improving factors of the present invention) into contact with a somatic cell in the step of nuclear reprogramming of the somatic cell. Here, the nuclear reprogramming of the somatic cell is achieved by transferring nuclear reprogramming substance(s) to the somatic cell; therefore, the present invention also provides a method of producing an iPS cell by bringing the factor(s) and nuclear reprogramming substance(s) into contact with a somatic cell. Herein, cases where iPS cells cannot be established by merely transferring nuclear reprogramming substance(s) alone to a somatic cell, but can be established by bringing nuclear reprogramming substance(s) along with the establishment efficiency improving factor(s) of the present invention into contact with a somatic cell, are also deemed as corresponding to "an improvement of establishment efficiency."

(a) Source of Somatic Cells

In the present invention, any cells other than germ cells of mammalian origin (e.g., humans, mice, monkeys, pigs, rats etc.) can be used as starting material for the production of iPS cells. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), contractile cells (e.g., smooth muscle cells), cells of the blood and the immune system (e.g., T lymphocytes), sense-related cells (e.g., rod cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells thereof (tissue progenitor cells) and the like. There is no limitation on the degree of cell differentiation, the age of the animal from which cells are collected and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as neural stem cells, hematopoietic stem cells, mesenchymal stem cells, and dental pulp stem cells.

The choice of mammal individual as a source of somatic cells is not particularly limited; however, when the iPS cells obtained are to be used for the regenerative medicine in humans, it is preferable, from the viewpoint of prevention of graft rejection to collect the somatic cells from the patient or another person with the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressant and the like. For example, it includes an HLA type wherein major HLAs (e.g., the three major loci of HLA-A, HLA-B and HLA-DR) are identical and the like (hereinafter the same meaning shall apply). When the iPS cells obtained are not to be administered (transplanted) to a human, but used as, for example, a source of cells for screening for evaluating a patient's drug susceptibility or adverse reactions, it is likewise desirable to collect the somatic cells from the patient or another person with the same genetic polymorphism correlating with the drug susceptibility or adverse reactions.

Before being subjected to the step of nuclear reprogramming, somatic cells separated from a mammal can be pre-cultured using a medium known per se suitable for the cultivation thereof, depending on the kind of the cells. Examples of such media include, but are not limited to, a minimal essential medium (MEM) containing about 5 to 20% fetal calf serum, Dulbecco's modified Eagle medium (DMEM), RPMI1640 medium, 199 medium, F12 medium and the like. When using, for example, a transfection reagent such as a cationic liposome in contacting the cell with the establishment efficiency improving factors of the present invention and nuclear reprogramming substance(s) (and another iPS cell establishment efficiency improver as required), it is sometimes preferable that the medium be previously replaced with a serum-free medium to prevent a reduction in the transfer efficiency.

(b) The Establishment Efficiency Improving Factors of the Present Invention

Cyclin D is a member of the cyclin protein family that is involved in regulating cell cycle progression. The synthesis of cyclin D is initiated during G1 phase and drives G1/S phase transition. In proliferating cells, cyclin D-CDK4/6 complex phosphorylates Rb, which can induce expression of some genes such as cyclin E important for S phase progression. Cyclin D family includes cyclin D1, cyclin D2 and cyclin D3.

Although the members of cyclin D family used in the present invention may be proteins derived from optionally chosen mammals (e.g., humans, mice, rats, monkeys, bovines, horses, pigs, dogs and the like) or nucleic acids that encode the same, proteins or nucleic acids of human or mouse origin are preferred. Information on the amino acid sequences and cDNA sequences of cyclin D1, cyclin D2 and cyclin D3 of human or mouse origin can be acquired by referring to the NCBI accession numbers shown in Table 1; those skilled in the art are easily able to isolate nucleic acids that encode the respective proteins on the basis of the cDNA sequence information, and to produce recombinant proteins as required.

TABLE 1

| Gene name | Human | | Mouse | |
| --- | --- | --- | --- | --- |
|  | cDNA | Protein | cDNA | Protein |
| cyclin D1 | NM_053056 | NP_444284 | NM_007631 | NP_031657 |
| cyclin D2 | NM_001759 | NP_001750 | NM_009829 | NP_033959 |
| cyclin D3 | NM_001136017 | NP_001129489 | NM_001081635 | NP_001075104 |
|  | NM_001136125 | NP_001129597 | NM_001081636 | NP_001075105 |
|  | NM_001136126 | NP_001129598 | NM_007632 | NP_031658 |
|  | NM_001760 | NP_001751 |  |  |

A natural or artificial mutant protein having an identity of 80% or more, preferably 90% or more, more preferably 95% or more, particularly preferably 97% or more, to each amino acid sequence shown above, and possessing a potential for improving iPS cell establishment efficiency equivalent to or greater than that of the wild-type protein and a nucleic acid that encodes the same, can also be utilized as the establishment efficiency improving factors of the present invention.

Out of members of cyclin D family (including nucleic acids that encode the same), any one kind alone may be used, and two kinds or more may be used in combination.

Transfer of cyclin D protein(s) to a somatic cell can be achieved using a method known per se for protein transfer into a cell, provided that the substance is a proteinous factor. Such methods include, for example, the method using a protein transfer reagent, the method using a protein transfer domain (PTD)- or cell penetrating peptide (CPP)-fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IM-GENEX); those based on a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactivated hemagglutinating virus of Japan) and the like. The transfer can be achieved per the protocols attached to these reagents, a common procedure being as described below. Cyclin D protein(s) is(are) diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as drosophila-derived AntP, HIV-derived TAT (Frankel, A. et al, *Cell* 55, 1189-93 (1988) or Green, M. & Loewenstein P. M. *Cell* 55, 1179-88 (1988)), Penetratin (Derossi, D. et al, *J. Biol. Chem.* 269, 10444-50 (1994)), Buforin II (Park, C. B. et al. *Proc. Natl Acad. Sci. USA* 97, 8245-50 (2000)), Transportan (Pooga, M. et al. *FASEB J.* 12, 67-77 (1998)), MAP (model amphipathic peptide) (Oehlke, J. et al. *Biochim. Biophys. Acta.* 1414, 127-39 (1998)), K-FGF (Lin, Y. Z. et al. *J. Biol. Chem.* 270, 14255-14258 (1995)), Ku70 (Sawada, M. et al. *Nature Cell Biol.* 5, 352-7 (2003)), Prion (Lundberg, P. et al. *Biochem. Biophys. Res. Commun.* 299, 85-90 (2002)), pVEC (Elmquist, A. et al. *Exp. Cell Res.* 269, 237-44 (2001)), Pep-1 (Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G L. *Cancer Res.* 60, 6551-6 (2000)), and HSV-derived VP22. CPPs derived from the PTDs include polyarginines such as 11R (*Cell Stem Cell*, 4, 381-384 (2009)) and 9R (*Cell Stem Cell*, 4, 472-476 (2009)).

A fusion protein expression vector incorporating a cDNA of cyclin D1, cyclin D2 or cyclin D3 and a PTD or CPP sequence is prepared to allow the recombinant expression of the fusion protein, and the fusion protein is recovered for use for transfer. This transfer can be achieved as described above, except that no protein transfer reagent is added.

Microinjection, a method of placing a protein solution in a glass needle having a tip diameter of about 1 μm, and injecting the solution into a cell, ensures the transfer of the protein into the cell.

Other useful methods of protein transfer include electroporation, the semi-intact cell method [Kano, F. et al Methods in Molecular Biology, Vol. 322, 357-365(2006)], transfer using the Wr-t peptide [Kondo, E. et al., Mol. Cancer Ther. 3(12), 1623-1630(2004)] and the like.

The protein transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 to 48 hours, preferably 12 to 24 hours.

The choice of nucleic acids that encode proteins of cyclin D family is not particularly limited. The nucleic acid may be a DNA or an RNA, or a DNA/RNA chimera, and is preferably a DNA. The nucleic acid may be double-stranded or single-stranded. In the case of double strands, the nucleic acid may be a double-stranded DNA, a double-stranded RNA or a DNA:RNA hybrid.

A nucleic acid encoding a protein of cyclin D family can, for example, be cloned from a cell or tissue [e.g., cells and tissues of thymus, bone marrow, spleen, brain, spinal cord, heart, skeletal muscle, kidney, lung, liver, pancreas or prostate, progenitor cells, stem cells or cancer cells of these cells, and the like] of a human or another mammal (e.g., mouse, rat, monkey, pig, dog and the like) by a conventional method.

Transfer of a nucleic acid encoding a protein of cyclin D family to a somatic cell can be achieved using a method of gene transfer to cells known per se. A nucleic acid that encodes a protein of cyclin D family is inserted into an appropriate expression vector containing a promoter capable of functioning in the host somatic cell. Useful expression vectors include, for example, viral vectors such as retrovirus, lentivirus, adenovirus, adeno-associated virus, herpes virus and Sendai virus, plasmids for the expression in animal cells (e.g., pA1-11, pXT1, pRc/CMV, pRc/RSV, pcDNAI/Neo) and the like.

A vector for this purpose can be chosen as appropriate according to the intended use of the iPS cell to be obtained. Useful vectors include adenovirus vector, plasmid vector, adeno-associated virus vector, retrovirus vector, lentivirus vector, Sendai virus vector, episomal vector and the like.

Examples of promoters used in expression vectors include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EFla promoter, the CAG promoter, the MoMuLV LTR, the CMV promoter, the SRa promoter and the like.

The expression vector may contain as desired, in addition to a promoter, an enhancer, a polyadenylation signal, a selectable marker gene, a SV40 replication origin and the like. Examples of selectable marker genes include the dihydrofolate reductase gene, the neomycin resistant gene, the puromycin resistant gene and the like.

A nucleic acid that encodes a protein of cyclin D family may be integrated alone into an expression vector, or along with one or more reprogramming genes into an expression vector. Preference is sometimes given to the former case when using a retrovirus or lentivirus vector, which offer high gene transfer efficiency, and to the latter case when using a plasmid, adenovirus, or episomal vector and the like, but there are no particular limitations.

In the context above, when a nucleic acid that encodes a protein of cyclin D family and one or more reprogramming genes are integrated in one expression vector, these genes can preferably be integrated into the expression vector via a sequence enabling polycistronic expression. By using a sequence enabling polycistronic expression, it is possible to more efficiently express a plurality of genes integrated in one expression vector. Useful sequences enabling polycistronic expression include, for example, the 2A sequence of foot-and-mouth disease virus (PLoS ONE3, e2532, 2008, Stem Cells 25, 1707, 2007), the IRES sequence (U.S. Pat. No. 4,937,190) and the like, with preference given to the 2A sequence.

An expression vector harboring a nucleic acid that encodes a protein of cyclin D family can, be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to the cell by a method suitable for each viral vector. For example, specific means using a retroviral vector are disclosed in WO2007/69666, *Cell,* 126, 663-676 (2006) and *Cell,* 131, 861-872 (2007); when a lentivirus vector is used, a disclosure is available in *Science,* 318, 1917-1920 (2007). When iPS cells are utilized as a source of cells for regenerative medicine, the expression (reactivation) of a protein of cyclin D family or the activation of an endogenous gene present in the vicinity of the site where the exogenous gene is integrated potentially increases the risk of carcinogenesis in tissues regenerated from differentiated cells of iPS cell derivation; therefore, a nucleic acid that encodes a protein of cyclin D family is preferably expressed transiently, without being integrated into the chromosome of the cells. From this viewpoint, use of an adenoviral vector, whose integration into chromosome is rare, is preferred. Specific means using an adenoviral vector is described in *Science,* 322, 945-949 (2008). Because an adeno-associated viral vector is also low in the frequency of integration into chromosome, and is lower than adenoviral vectors in terms of cytotoxicity and inflammation-inducibility, it can be mentioned as another preferred vector. Because Sendai viral vector is capable of being stably present outside the chromosome, and can be degraded and removed using an siRNA as required, it is preferably utilized as well. Regarding a Sendai viral vector, one described in *J. Biol. Chem.,* 282, 27383-27391 (2007) and JP-3602058 B can be used.

When a retroviral vector or a lentiviral vector is used, even if silencing of the transgene has occurred, it possibly becomes reactivated later; therefore, for example, a method can be used preferably wherein a nucleic acid that encodes a protein of cyclin D family is cut out using the Cre/loxP system, when becoming unnecessary. That is, with loxP sequences arranged on both ends of the nucleic acid in advance, after iPS cells are induced, the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivating (SIN) LTR prepared by deleting the sequence, or substituting the sequence with a polyadenylation sequence such as of SV40. Specific means using the Cre-loxP system and SIN LTR is disclosed in Soldner et al., *Cell,* 136: 964-977 (2009), Chang et al., *Stem Cells,* 27: 1042-1049 (2009) and the like.

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Specific means using a plasmid as a vector are described in, for example, *Science,* 322, 949-953 (2008) and the like.

When a plasmid vector, an adenovirus vector and the like are used, the transfection can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature,* 458: 771-775 (2009), Woltjen et al., *Nature,* 458: 766-770 (2009).

Another preferable non-integration type vector is an episomal vector, which is autonomously replicable outside the chromosome. Specific means with the use of an episomal vector is described by Yu et al. in *Science,* 324, 797-801 (2009). As appropriate, an expression vector in which a nucleic acid that encodes a protein of cyclin D family is inserted into an episomal vector having loxP sequences placed in the same orientation on the 5' and 3' sides of the vector constituent essential for the replication of the episomal vector can be constructed and introduced into a somatic cell.

Examples of the episomal vector include a vector comprising as a vector component a sequence derived from EBV, SV40 and the like necessary for self-replication. The vector component necessary for self-replication is specifically exemplified by a replication origin and a gene that encodes a protein that binds to the replication origin to control the replication; examples include the replication origin oriP and the EBNA-1 gene for EBV, and the replication origin on and the SV40 large T antigen gene for SV40.

The episomal expression vector harbors a promoter that controls the transcription of a nucleic acid that encodes a protein of cyclin D family. Useful promoters include those mentioned above. The episomal expression vector, like the aforementioned vectors, may further contain as desired an enhancer, a polyA addition signal, a selection marker gene and the like. Examples of useful selection marker genes include the dihydrofolate reductase gene, the neomycin resistance gene and the like.

The loxP sequences useful in the present invention include, in addition to the bacteriophage P1-derived wild type loxP sequence, optionally chosen mutant loxP sequences capable of deleting the sequence flanked by the loxP sequence by recombination when placed in the same orientation at positions flanking a vector component necessary for the replication of the introduced gene. Examples of such mutant loxP sequences include lox71, mutated in 5' repeat, lox66, mutated in 3' repeat, and lox2272 and lox511, mutated in spacer portion. Although the two loxP sequences placed on the 5' and 3' sides of the vector component may be identical or not, the two mutant loxP sequences mutated in spacer portion must be identical (e.g., a pair of lox2272 sequences, a pair of lox511 sequences). Preference is given to a combination of a mutant loxP sequence mutated in 5' repeat (e.g., lox71) and a mutant loxP sequence mutated in 3' repeat (e.g., lox66). In this case, the loxP sequences remaining on the chromosome have double mutations in the repeats on the 5' side and 3' side as a result of recombination, and are therefore unlikely to be recognized by Cre recombinase, thus reducing the risk of causing a deletion mutation in the chromosome due to unwanted recombination. When the mutant loxP sequences lox71 and lox66 are used in combination, each may be placed on any of the 5' and 3' sides of the aforementioned vector component, but it is necessary that the mutant loxP sequences be inserted in an orientation such that the mutated sites would be located at the outer ends of the Tespective loxP sequences. Although a preferred episomal vector of the present invention is a self-removal vector early shedding from the cell even without being acted on by Cre recombinase, there are possibly exceptional cases where longer time is taken for the episomal vector to be shed from the cell. It is preferable, therefore, that the loxP sequences be designed in preparation for risks such as unwanted recombination due to Cre recombinase treatment.

Each of the two loxP sequences is placed in the same orientation on the 5' and 3' sides of a vector constituent essential for the replication of the introduced gene (i.e., a replication origin, or a gene sequence that encodes a protein that binds to the replication origin to control the replication). The vector constituent flanked by the loxP sequences may be either the replication origin or a gene sequence that encodes a protein that binds to a replication origin to control the replication, or both.

The episomal vector allows the vector to be introduced into the cell using, for example, the lipofection method, liposome method, electroporation method, calcium phosphate co-precipitation method, DEAE dextran method, microinjection method, gene gun method and the like. Specifically, for example, methods described in *Science*, 324: 797-801 (2009) and elsewhere can be used.

Whether or not the vector component necessary for the replication of the introduced gene has been removed from the iPS cell can be confirmed by performing a Southern blot analysis or PCR analysis using a nucleic acid comprising a nucleotide sequence in the vector component as a probe or primer, with the episome fraction isolated from the iPS cell, as a template, and determining the presence or absence of a band or the length of the band detected. The episome fraction can be prepared by a method well known in the art; for example, methods described in *Science*, 324: 797-801 (2009) and elsewhere can be used.

(c) Nuclear Reprogramming Substances

As used herein, "a nuclear reprogramming substance" can include a proteinous factor, a nucleic acid that encodes the same (including a form integrated in a vector) or a low molecular weight compound, as long as it can induce an iPS cell from a somatic cell upon its contact with the somatic cell together with the iPS cell establishment efficiency improving factors of the present invention. When the nuclear reprogramming substance is a proteinous factor or a nucleic acid that encodes the same, the following combinations, for example, are preferable (hereinafter, only the names for proteinous factors are shown).

(1) Oct3/4, Klf4, c-Myc
(2) Oct3/4, Klf4, c-Myc, Sox2 (Sox2 is replaceable with Sox1, Sox3, Sox15, Sox17 or Sox18; Klf4 is replaceable with Klf1, Klf2 or Klf5; c-Myc is replaceable with T58A (active mutant), N-Myc, or L-Myc)
(3) Oct3/4, Klf4, c-Myc, Sox2, Fbx15, Nanog, Eras, ECAT15-2, Tcll, β-catenin (active mutant S33Y)
(4) Oct3/4, Klf4, c-Myc, Sox2, TERT, SV40 Large T antigen (hereinafter SV40LT)
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmil [For more information on the factors shown above, see WO 2007/069666 (for information on replacement of Sox2 with Sox18 and replacement of Klf4 with Klf1 or Klf5 in the combination (2) above, see *Nature Biotechnology*, 26, 101-106 (2008)); for the combination "Oct3/4, Klf4, c-Myc, Sox2", see also *Cell*, 126, 663-676 (2006), Cell, 131, 861-872 (2007) and the like; for the combination "Oct3/4, Klf2 (or Klf5), c-Myc, Sox2", see also *Nat. Cell Biol.*, 11, 197-203 (2009); for the combination "Oct3/4, Klf4, c-Myc, Sox2, hTERT, SV40 LT", see also *Nature*, 451, 141-146 (2008).]
(9) Oct3/4, Klf4, Sox2 (see *Nature Biotechnology*, 26, 101-106 (2008))
(10) Oct3/4, Sox2, Nanog, Lin28 (see *Science*, 318, 1917-1920 (2007))
(11) Oct3/4, Sox2, Nanog, Lin28, hTERT, SV40LT (see *Stem Cells*, 26, 1998-2005 (2008))
(12) Oct3/4, Klf4, c-Myc, Sox2, Nanog, Lin28 (see *Cell Research* (2008) 600-603)
(13) Oct3/4, Klf4, c-Myc, Sox2, SV40LT (see also *Stem Cells*, 26, 1998-2005 (2008))
(14) Oct3/4, Klf4 (see *Nature* 454:646-650 (2008), Cell Stem Cell, 2:525-528 (2008)))
(15) Oct3/4, c-Myc (see *Nature* 454:646-650 (2008))
(16) Oct3/4, Sox2 (see Nature, 451, 141-146 (2008), WO2008/118820)
(17) Oct3/4, Sox2, Nanog (see WO2008/118820)
(18) Oct3/4, Sox2, Lin28 (see WO2008/118820)
(19) Oct3/4, Sox2, c-Myc, Esrrb (Here, Esrrb can be substituted by Esrrg, see *Nat. Cell Biol.*, 11, 197-203 (2009)) substituted by Esrrg, see *Nat. Cell Biol.*, 11, 197-203 (2009))
(20) Oct3/4, Sox2, Esrrb (see *Nat. Cell Biol.*, 11, 197-203 (2009))
(21) Oct3/4, Klf4, L-Myc (see *Proc. Natl. Acad. Sci. USA.*, 107, 14152-14157 (2010))
(22) Oct3/4, Nanog
(23) Oct3/4 (*Cell* 136: 411-419 (2009); *Nature*, 08436, doi:10.1038 published online(2009))
(24) Oct3/4, Klf4, c-Myc, Sox2, Nanog, Lin28, SV40LT (see *Science*, 324: 797-801 (2009))

In (1)-(24) above, Oct3/4 may be replaced with another member of the Oct family, for example, Oct1A, Oct6 or the like. Sox2 (or Sox1, Sox3, Sox15, Sox17, Sox18) may be replaced with another member of the Sox family, for example, Sox7 or the like. Furthermore, in (1) to (24) above, when c-Myc or Lin28 is included as a nuclear reprogramming factor, L-Myc or Lin28B can be used in place of c-Myc or Lin28, respectively.

Any combination that does not fall in (1) to (24) above but comprises all the constituents of any one of (1) to (24) above and further comprises an optionally chosen other substance can also be included in the scope of "nuclear reprogramming substances" in the present invention. Provided that the somatic cell to undergo nuclear reprogramming is endogenously expressing one or more of the constituents of any one of (1) to (24) above at a level sufficient to cause nuclear reprogramming, a combination of only the remaining constituents excluding the one or more constituents can also be included in the scope of "nuclear reprogramming substances" in the present invention.

Of these combinations, a combination of at least one, preferably two or more, more preferably three or more, selected from among Oct3/4, Sox2, Klf4, c-Myc or L-Myc, Nanog, Lin28 or Lin28B, and SV40LT, is a preferable nuclear reprogramming substance.

Particularly, when the iPS cells obtained are to be used for therapeutic purposes, a combination of the three factors Oct3/4, Sox2 and Klf4 [combination (9) above] or a combination of the four factors Oct3/4, Sox2, Klf4 and L-Myc [combination (2) above] are preferably used. When the iPS cells obtained are not to be used for therapeutic purposes (e.g., used as an investigational tool for drug discovery screening and the like), in addition to the three factors consisting of Oct3/4, Sox2 and Klf4 and the four factors consisting of Oct3/4, Sox2, Klf4 and L-Myc, four factors consisting of Oct3/4, Sox2, Klf4 and c-Myc, five or six factors consisting of Oct3/4, Sox2, Klf4 and c-Myc/L-Myc as well as Nanog and/or Lin28/Lin28b, or six or seven factors consisting of the above five or six factors and additional SV40 Large T antigen are exemplified.

Information on the mouse and human cDNA sequences of the aforementioned nuclear reprogramming substances is available with reference to the NCBI accession numbers mentioned in WO 2007/069666 (in the publication, Nanog is described as ECAT4. Mouse and human cDNA sequence information on Lin28, Lin28b, Esrrb, Esrrg, L-Myc can be acquired by referring to the following NCBI accession numbers, respectively); those skilled in the art are easily able to isolate these cDNAs.

| Name of gene | Mouse | Human |
| --- | --- | --- |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |

A proteinous factor for use as a nuclear reprogramming substance can be prepared by inserting the cDNA obtained into an appropriate expression vector, introducing the vector into a host cell, and recovering the recombinant proteinous factor from the cultured cell or its conditioned medium. Meanwhile, when the nuclear reprogramming substance used is a nucleic acid that encodes a proteinous factor, the cDNA obtained is inserted into a viral vector, episomal vector, or plasmid vector to construct an expression vector, and the vector is subjected to the step of nuclear reprogramming. As appropriate, the above-mentioned Cre-loxP system or piggyBac transposon system can be utilized. When two or more nucleic acids encoding proteinous factors are introduced into a cell, respective nucleic acids can be carried in separate vectors. Alternatively, a polycistronic vector can be constructed by ligating a plurality of nucleic acids in tandem. In latter, it is preferable that 2A self-cleaving peptide from a foot-and-mouth disease virus (Science, 322, 949-953, 2008) is ligated between the nucleic acids to allow for an efficient polycistronic expression.

Contact of a nuclear reprogramming substance with a somatic cell can be achieved as with a protein of cyclin D family (a) when the substance is a proteinous factor; as with the aforementioned nucleic acid that encodes a protein of cyclin D family (b) when the substance is a nucleic acid that encodes the proteinous factor of (a).

(d) Other iPS Cell Establishment Efficiency Improvers

In recent years, various substances that improve the efficiency of establishment of iPS cells, which has traditionally been low, have been proposed one after another. When brought into contact with a somatic cell together with the aforementioned iPS cell establishment efficiency improving factors of the present invention, these other establishment efficiency improvers are expected to further raise the efficiency of establishment of iPS cells.

Examples of other iPS cell establishment efficiency improvers include, but are not limited to, histone deacetylase (HDAC) inhibitors [e.g., valproic acid (VPA) (Nat. Biotechnol., 26(7): 795-797 (2008)], low-molecular inhibitors such as trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], DNA methyltransferase inhibitors (e.g., 5'-azacytidine) [Nat. Biotechnol., 26(7): 795-797 (2008)], G9a histone methyltransferase inhibitors [e.g., low-molecular inhibitors such as BIX-01294 (Cell Stem Cell, 2: 525-528 (2008)], nucleic acid-based expression inhibitors such as siRNAs and shRNAs against G9a [e.g., G9a siRNA (human) (Santa Cruz Biotechnology) and the like) and the like], L-channel calcium agonists (e.g., Bayk8644) [Cell Stem Cell, 3, 568-574 (2008)], p53 inhibitors [e.g., siRNA, shRNA, dominant negative mutant and the like against p53 (Cell Stem Cell, 3, 475-479 (2008); Nature 460, 1132-1135 (2009))], UTF1 [Cell Stem Cell, 3, 475-479 (2008)], Wnt Signaling (e.g., soluble Wnt3a) [Cell Stem Cell, 3, 132-135 (2008)], 2i/LIF [2i is an inhibitor of mitogen-activated protein kinase signaling and glycogen synthase kinase-3, PloS Biology, 6(10), 2237-2247 (2008)], ES cell-specific miRNA (for example, miR-302-367 cluster (Mol. Cell. Biol. doi:10.1128/MCB.00398-08), miR-302 (RNA (2008) 14: 1-10), miR-291-3p, miR-294 and miR-295 (Nat. Biotechnol. 27: 459-461 (2009)) and the like. As mentioned above, the nucleic acid-based expression inhibitors may be in the form of expression vectors harboring a DNA that encodes an siRNA or shRNA.

Among the constituents of the aforementioned nuclear reprogramming substances, SV40 large T and the like, for example, can also be included in the scope of iPS cell establishment efficiency improvers because they are deemed not essential, but auxiliary, factors for somatic cell nuclear reprogramming. In the situation of the mechanisms for nuclear reprogramming remaining unclear, the auxiliary factors, which are not essential for nuclear reprogramming, may be conveniently considered as nuclear reprogramming substances or iPS cell establishment efficiency improvers.

Hence, because the somatic cell nuclear reprogramming process is understood as an overall event resulting from contact of nuclear reprogramming substance(s) and iPS cell establishment efficiency improver(s) with a somatic cell, it seems unnecessary for those skilled in the art to always distinguish between the nuclear reprogramming substance and the iPS cell establishment efficiency improver.

Contact of an iPS cell establishment efficiency improver with a somatic cell can be achieved as with a protein of cyclin D family (a) when the improver is a proteinous factor; as with the aforementioned nucleic acid that encodes a protein of cyclin D family (b) when the improver is a nucleic acid that encodes the proteinous factor of (a).

An iPS cell establishment efficiency improver including a cyclin D protein or a nucleic acid encoding the same may be brought into contact with a somatic cell simultaneously with a nuclear reprogramming substance, or either one may be contacted in advance, as far as the efficiency of establishment of iPS cells from the somatic cell is significantly improved, compared with the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, when a nuclear reprogramming substance and an iPS cell establishment efficiency improver are both used in the form of a viral or plasmid vector, for example, both may be simultaneously introduced into the cell.

(e) Improving Establishment Efficiency by Culture Conditions iPS cell establishment efficiency can further be improved by culturing the cells under hypoxic conditions in the nuclear reprogramming process for somatic cells (*Cell Stem Cell*, 5(3): 237-241 (2009); WO 2010/013845). As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.9% or more and the like), or 1% or more (e.g., 1.1% or more, 1.2% or more, 1.3% or more, 1.4% or more and the like).

Although any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). Although the culture may be' started before the somatic cell is contacted with cyclin D protein(s) or nucleic acid(s) encoding the same and nuclear reprogramming substance, or at the same time as the contact, or after the contact, it is preferable, for example, that the culture under hypoxic conditions be started just after the somatic cell is contacted with cyclin D protein(s) or nucleic acid(s) encoding the same and nuclear reprogramming substance, or at a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on the choice of nuclear reprogramming substance used, iPS cell establishment efficiency under normal oxygen concentration conditions and the like.

(f) Selection and Confirmation of iPS Cell

After being contacted with nuclear reprogramming substance(s) and the iPS cell establishment efficiency improving factors of the present invention (and other iPS cell establishment efficiency improving factors), the cell can be cultured under conditions suitable for the cultivation of, for example, ES cells. In the case of mouse cells, the cultivation is carried out with the addition of Leukemia Inhibitory Factor (LIF) as a differentiation suppressor to an ordinary medium. Meanwhile, in the case of human cells, it is desirable that basic fibroblast growth factor (bFGF) and/or stem cell factor (SCF) be added in place of LIF. Usually, the cells are cultured in the co-presence of mouse embryo-derived fibroblasts (MEF) treated with radiation or an antibiotic to terminate the cell division thereof, as feeder cells. MEF in common use as feeders include the STO cell and the like; for induction of an iPS cell, the SNL cell [McMahon, A. P. & Bradley, A. Cell 62, 1073-1085 (1990)] and the like are commonly used. Co-culture with these feeder cells may be started before contact of the nuclear reprogramming substance(s) and the iPS cell establishment efficiency is improving factors of the present invention, at the time of the contact, or after the contact (e.g., 1-10 days later).

A candidate colony of iPS cells can be selected by a method with drug resistance and reporter activity as indicators, and also by a method based on visual examination of morphology. As an example of the former, a colony positive for drug resistance and/or reporter activity is selected using a recombinant somatic cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Examples of such recombinant somatic cells include MEFs or TTFs from a mouse having the βgeo (which encodes a fusion protein of β-galactosidase and neomycin phosphotransferase) gene knocked-in to the Fbx15 locus [Takahashi & Yamanaka, Cell, 126, 663-676 (2006)], MEFs or TTFs from a transgenic mouse having the green fluorescent protein (GFP) gene and the puromycin resistance gene integrated in the Nanog locus [Okita et al., Nature, 448, 313-317 (2007)] and the like. Meanwhile, examples of the method of selecting candidate colonies based on visual examination of morphology include, the method described by Takahashi et al. in Cell, 131, 861-872 (2007). Although the method using reporter cells is convenient and efficient, it is desirable from the viewpoint of safety that colonies be selected by visual examination when iPS cells are prepared for the purpose of human treatment.

The identity of the cells of a selected colony as iPS cells can be confirmed by positive responses to a Nanog (or Oct3/4) reporter (puromycin resistance, GFP positivity and the like) as well as by the formation of a visible ES cell-like colony, as described above. However, to ensure higher accuracy, it is possible to perform tests such as alkaline phosphatase staining, analyzing the expression of various ES-cell-specific genes, and transplanting the cells selected to a mouse to confirm the formation of teratomas.

When a nucleic acid that encodes a protein of cyclin D family is introduced into a somatic cell, the iPS cell obtained is a novel cell distinct from conventionally known iPS cells because of the containment of the exogenous nucleic acid. In particular, when the exogenous nucleic acid is introduced into the somatic cell using a retrovirus, lentivirus or the like, the exogenous nucleic acid is usually integrated in the genome of the iPS cell obtained, so that the phenotype of containing the exogenous nucleic acid is stably retained.

(g) Use of iPS Cell

The iPS cells thus established can be used for various purposes. For example, by utilizing a method of differentiation induction reported with respect to ES cells (for example, see JP 2002-291469 as a method for inducing differentiation into nerve stem cells, JP 2004-121165 as a method for inducing differentiation into pancreatic stem-like cells, JP 2003-505006 as a method for inducing differentiation into hematopoietic cells, JP 2003-523766 as a differentiation induction method via embryonic body formation), differentiation into various cells (e.g., myocardial cells, blood cells, nerve cells, vascular endothelial cells, insulin-secreting cells and the like) from iPS cells can be induced. Therefore, inducing iPS cells using a somatic cell collected from a patient or another person of the same or substantially the same HLA type would enable stem cell therapy by autogeneic or allogeneic transplantation, wherein the iPS cells are differentiated into desired cells (that is, cells of an affected organ of the patient, cells that have a therapeutic effect on disease, and the like), which are transplanted to the patient. Furthermore, because functional cells (e.g., hepatocytes) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

The present invention is hereinafter described in further detail by means of the following examples, to which, however, the invention is never limited.

EXAMPLES

Example 1

Consideration of Effect of p53-p21 Pathway-Related Factors on iPS Cell Establishment (1)

Whether or not various factors (PCNA, CDK2, Cyclin D1) present in the p53-p21 pathway influence the iPS cell establishment efficiency was examined.

The following genes were introduced by retrovirus into fetal fibroblasts (MEF) obtained from Nanog reporter mouse having Nanog-GFP-IRES-Puro$^r$ (Okita K. et al, Nature 448, 313-317(2007)).
1) mouse-derived Oct3/4, Sox2, Klf4, c-Myc, DsRed
2) mouse-derived Oct3/4, Sox2, Klf4, c-Myc, PCNA
3) mouse-derived Oct3/4, Sox2, Klf4, c-Myc, CDK2
4) mouse-derived Oct3/4, Sox2, Klf4, c-Myc, Cyclin D1

The retrovirus was prepared by separately introducing a retrovirus expression vector (Cell, 126, 663-676 (2006)) into Plat-E cells (Morita, S. et al., Gene Ther. 7, 1063-1066) seeded in a 6-well culture plate (Falcon) at $0.6 \times 10^6$/well the previous day. As the culture medium, DMEM/10% FCS (DMEM (Nacalai tesque), 10% FCS, 50 units penicillin and 50 µg/ml streptomycin) was used, and the cells were cultured at 37° C., 5% $CO_2$. For introduction of the vector, FuGene6 transfection reagent (Roche, 4.5 µL) was added to Opti-MEM I Reduced-Serum Medium (Invitrogen, 100 µL), and the mixture was left standing at room temperature for 5 min. Thereafter, each expression vector was added by 1.5 µg, and the mixture was further left standing at room temperature for 15 min and added to the culture medium of Plat-E. On day 2, the supernatant of Plat-E was changed to a fresh medium, and the culture supernatant was collected on day 3 and filtered through a 0.45 µm sterile filter (Whatman). Polybrene (Nacalai) was added to 4 µg/mL to give a virus solution.

Then, MEF (passage 3) was seeded at $1.0 \times 10^5$/well in a 6-well culture plate (Falcon) coated with 0.1% gelatin (Sigma). As the culture medium, DMEM/10% FCS was used, and the cells were cultured at 37° C., 5% $CO_2$. The next day, each retrovirus solution was added with the combination shown in the aforementioned 1)-4), and the cells were infected overnight to introduce the genes.

On day 3 from the viral infection, the medium for MEF was removed, and a medium for ES cells was added. On day 5, the medium was removed, PBS (1 mL) was added to rinse the cells. After removing PBS, 0.25% trypsin/1 mM EDTA (Invitrogen) was added, and the mixture was reacted at 37° C. for about 5 min. Floating cells were suspended in ES cell medium and 5000 cells were plated in a 100 mm dish plated with STO feeder cells treated by mitomycin C. Thereafter, the ES cell medium was exchanged every 2 days.

The cells were counted when replating on day 5 from the infection, and the results are shown in FIG. 1 (left). In addition, the cells were replated in a $5 \times 10^3$ cells/100 mm dish and GFP positive colonies were counted on day 24 from the infection. The results are shown in FIG. 1 (right). Even when PCNA, CDK2 or Cyclin D1 was added to the 4 genes, a cell proliferation promoting effect was not observed (FIG. 1, left). However, when Cyclin D1 was added, a remarkable increase in the number of iPS cell colonies was observed (FIG. 1, right). From the above-mentioned results, it is clear that Cyclin D1 increases iPS cell establishment efficiency, and this action was suggested to be primarily attributable to actions other than cell proliferation.

Example 2

Consideraton of Effect for p53-p21 Pathway-Related Factors on iPS Cell Establishment (2)

An experiment similar to that of Example 1 was carried out by a combination of 3 genes (Oct3/4, Sox2, Klf4) instead of the 4 genes, and respective genes (PCNA, CDK2, Cyclin D1) of p53-p21 pathway.

Figure 2:
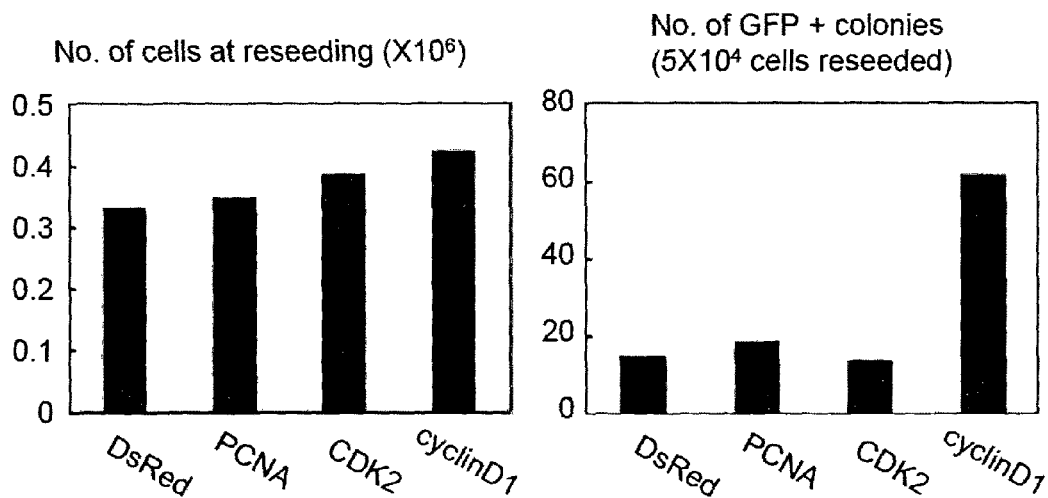
FIG. 2 shows graphs presenting the results of Example 2. The vertical axis of the left drawing shows the total number of cells, and the vertical axis of the right drawing shows the number of GFP positive colonies (iPS colony number). The horizontal axes show combinations of Oct3/4, Sox2 and Klf4 genes and respective genesshown in the horizontal axes.

The cells were counted when replating on day 5 from the infection, and the results are shown in FIG. 2 (left). In addition, the cells were replated in a $5 \times 10^4$ cells/100 mm dish and GFP positive colonies were counted on day 30 from the infection. The results are shown in FIG. 2 (right). As in Example 1, even when PCNA, CDK2 or Cyclin D1 was added to the 3 genes, a remarkable cell proliferation promoting effect was not observed (FIG. 2, left). However, when Cyclin D1 was added, a remarkable increase in the number of iPS cell colonies was observed (FIG. 2, right). From the above-mentioned results, it is clear that iPS cell establishment efficiency increases not only in the 4 genes but also the 3 genes by the addition of Cyclin D1, and this action was suggested to be primarily attributable to actions other than cell proliferation.

Example 3

Consideration of Effect of Cyclin D Family on iPS Cell Establishment

Whether or not Cyclin D2 and Cyclin D3, which are factors belonging to Cyclin D family, have an iPS cell establishment efficiency increasing effect similar to that of Cyclin D1 was examined. The experiment was carried out in the same manner as in Example 2, by a combination of 3 genes (Oct3/4, Sox2, Klf4) and respective genes (Cyclin D1, Cyclin D2, Cyclin D3) of Cyclin D family.

Figure 3:
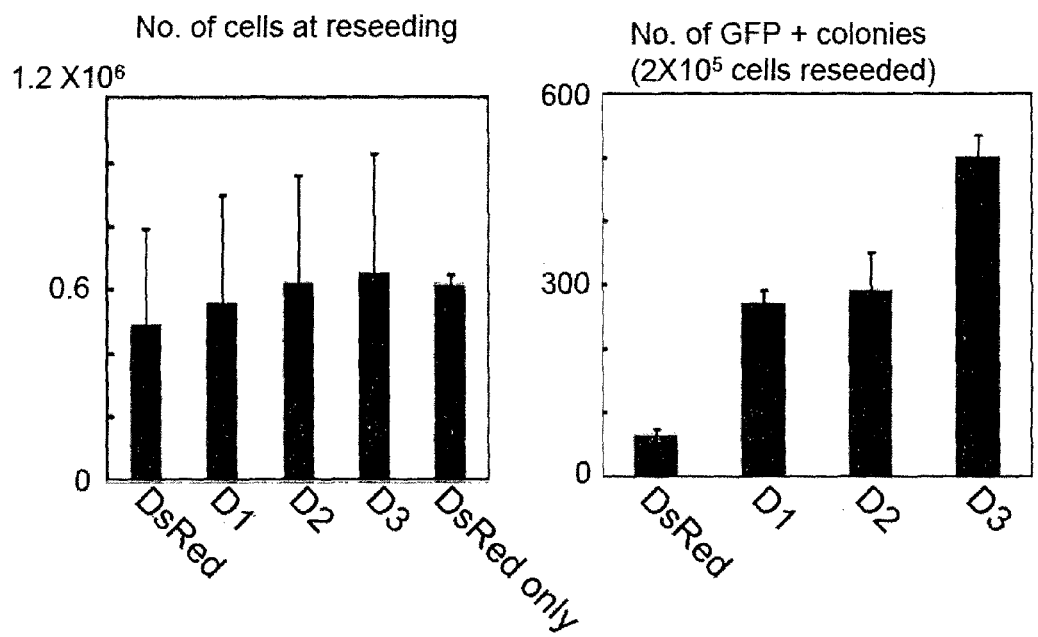
FIG. 3 shows graphs presenting the results of Example 3. The vertical axis of the left drawing shows the total number of cells, and the vertical axis of the right drawing shows the number of GFP positive colonies (iPS colony number). The horizontal axes show combinations of Oct3/4, Sox2 and Klf4 genes and respective genes shown in the horizontal axes.

The cells were counted when replating on day 5 from the infection, and the results are shown in FIG. 3 (left). In addition, the cells were replated in a $2 \times 10^5$ cells/100 mm dish and GFP positive colonies were counted on day 28 from the infection. The results are shown in FIG. 3 (right). As the results, average values of three experiments are shown. Even when Cyclin D1, Cyclin D2 or Cyclin D3 was added to the 3 genes, a remarkable cell proliferation promoting effect was not observed (FIG. 3, left). On the other hand, when Cyclin D2 or Cyclin D3 was added to the 3 genes, a remarkable increase in the number of iPS cell colonies was observed (FIG. 3, right) as with Cyclin D1. From the above-mentioned results, it is clear that not only Cyclin D1 but also Cyclin D2 and Cyclin D3 increase iPS cell establishment efficiency, and this action was suggested to be primarily attributable to actions other than cell proliferation.

Example 4

Expression in Reprogramming Process of Endogenous Cyclin D1

Figure 4:
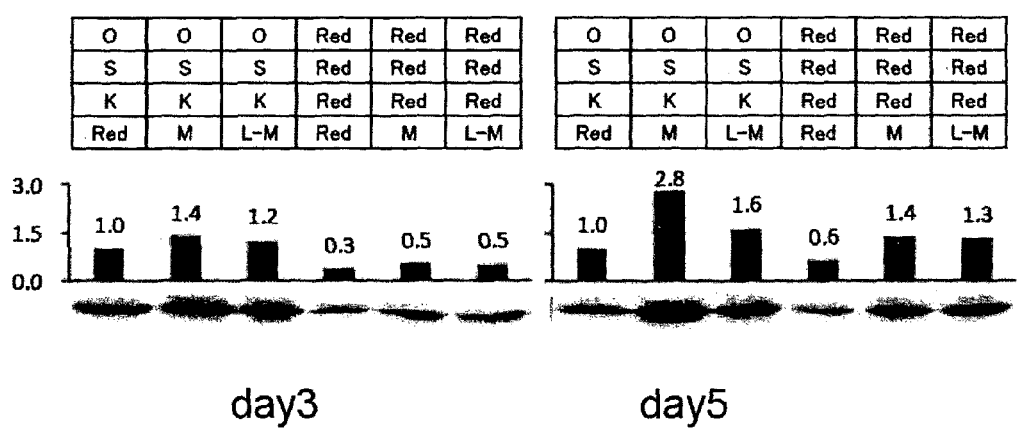
FIG. 4 shows graphs presenting the results of Example 4. The tables in the drawing show combinations of respective genes. The vertical axes of the graphs show values relative to the value of Western blot (density of band) after introduction of Oct3/4, Sox2 and Klf4 as 1.

Expression of endogenous Cyclin D1 in nuclear reprogramming process was examined. In the same manner as in Example 1, the following genes were introduced by retrovirus into MEF obtained from Nanog reporter mouse.
(1) mouse-derived Oct3/4, Sox2, Klf4, DsRed
(2) mouse-derived Oct3/4, Sox2, Klf4, c-Myc
(3) mouse-derived Oct3/4, Sox2, Klf4, L-Myc
(4) mouse-derived c-Myc, DsRed
(5) mouse-derived L-Myc, DsRed On day 3 and day 5 from the infection, endogenous Cyclin D1 was detected by Western blot according to a conventional method and the results are shown in FIG. 4. FIG. 4 shows values relative to the value (density of band) after introduction of Oct3/4, Sox2 and Klf4 as 1. As shown in FIG. 4, since reprogramming induction by the 3 genes (Oct3/4, Sox2, Klf4) or the 4 genes (Oct3/4, Sox2, Klf4, c-Myc or Oct3/4, Sox2, Klf4, L-Myc) resulted in increased expression amount of endogenous Cyclin D1, it is clear that Cyclin D1 expression is induced in an early stage of reprogramming. The increased expression of Cyclin D1 was also detected by single introduction of c-Myc or L-Myc.

Example 5

Consideration of Effect of Cyclin D1 on Human iPS Cell Establishment

Whether or not Cyclin D1 has an effect on human iPS cell establishment was examined.

Mouse ecotropic virus receptor Slc7a1 gene was expressed in skin-derived fibroblasts (HDF: cell name 1503) of an adult human (white female, 73-year-old) using lentivirus (pLenti6/UbC-Slc7a1), according to the method described in Takahashi, K. et al., *Cell,* 131: 861-872 (2007). The following genes were introduced by retrovirus into these cells ($1 \times 10^5$ cells/well, 6-well plate), according to the method described in Takahashi, K. et al., *Cell,* 131: 861-872 (2007), and the number of the resultant iPS cell colonies was compared to that obtained by introduction of 4 genes (Oct3/4, Sox2, Klf4, c-Myc).
1) human-derived Oct3/4, Sox2, Klf4, c-Myc, mouse-derived natural Cyclin D1
2) human-derived Oct3/4, Sox2, Klf4, c-Myc, mouse-derived T156A Cyclin D1
3) human-derived Oct3/4, Sox2, Klf4, c-Myc, mouse-derived T286A Cyclin D1

Here, the "T156A Cyclin D1" is an inactive mutant wherein the 156th threonine of Cyclin D1 has been substituted by alanine (inactive mutant Cyclin D1). While Cyclin D1 has an action to transfer the cell cycle to S-phase, T156A Cyclin D1 is known to be attenuated in this action.

In addition, the "T286A Cyclin D1" is a stable mutant of Cylcin D1, which is obtained by substituting the 286th threonine of Cyclin D1 to alanine, and resists removal from the nucleus, resulting in resistance to degradation by proteosome.

Figure 5:
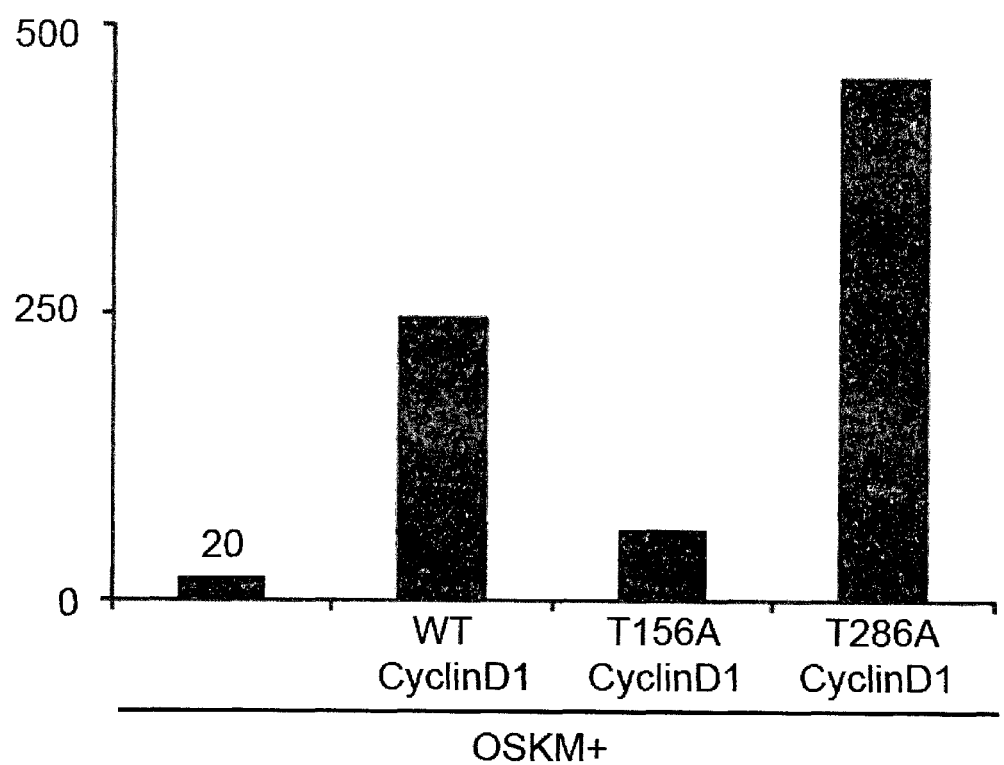
FIG. 5 shows a graph presenting the results of Example 5. The vertical axis of the drawing shows the number of iPS cell colonies. The horizontal axis shows combinations of Oct3/4, Sox2, Klf4 and c-Myc genes and respective genes shown in the horizontal axis.

The cells were collected on day 7 from the viral infection, and replated on feeder cells ($0.5 \times 10^5$ cells/100 mm dish). As the feeder cells, mitotically inactivated SNL cells by treatment with mitomycin C (McMahon, A. P. & Bradley, A. *Cell* 62, 1073-1085 (1990)) were used. From day 10 from the infection, the cells were cultured in a primate ES cell culture medium (ReproCELL) supplemented with 4 ng/ml recombinant human bFGF (WAKO). iPS cell colonies were counted on day 24 from the infection. The results are shown in FIG. 5. By the addition of wild Cyclin D1 to the 4 genes, the number of iPS cell colonies dramatically increased. The effect was suppressed when T156A Cyclin D1, which is a dominant-negative mutant, was used and further increased when T286A Cyclin D1, a stable mutant, was used. From the above, it is clear that Cyclin D1 also shows effect on human cells.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

This application is based on U.S. provisional patent application No. 61/410,178, the content of which is hereby incorporated by reference.

The invention claimed is:

1. A method of producing mammalian iPS cells, comprising
introducing into a mammalian somatic cell (a) expression vectors(s) comprising nucleic acids that encode nuclear reprogramming substances and (b) an expression vector comprising a nucleic acid that encodes a cyclin D family member, and
culturing the mammalian somatic cell to form a colony of reprogrammed cells exhibiting characteristics of pluripotency,
wherein the nuclear reprogramming substances comprise:
(i) Oct3/4,
(ii) a member of the Sox family selected from the group consisting of Sox1, Sox2, Sox3, Sox15, and Sox17, and
(iii) a member of the Klf family selected from the group consisting of Klf1, Klf2, Klf4 and Klf5.

2. The method according to claim 1, wherein the nuclear reprogramming substances further comprise:
(iv) a member of the Myc family-selected from the group consisting of c-Myc, L-Myc and N-Myc.

3. The method according to claim 1, wherein the nuclear reprogramming substances comprise Oct3/4, Sox2 and Klf4.

4. The method according to claim 2, wherein the nuclear reprogramming substances comprise Oct3/4, Sox2, Klf4 and c-Myc.

5. The method according to claim 2, wherein the nuclear reprogramming substances comprise Oct3/4, Sox2, Klf4 and L-Myc.

6. The method of claim 1, wherein the to cyclin D family member is selected from the group consisting of cyclin D1, cyclin D2 and cyclin D3.

7. An agent for inducing an iPS cell from a somatic cell, comprising a factor selected from the group consisting of proteins belonging to cyclin D family and nucleic acids that encode the same, and nuclear reprogramming substances, wherein the nuclear reprogramming substances comprise:
(i) Oct3/4 or a nucleic acid that encodes the same;
(ii) a member of the Sox family selected from the group consisting of Sox1, Sox2, Sox3, Sox15, and Sox17 or a nucleic acid that encodes the same, and
(iii) a member of the Klf family selected from the group consisting of Klf1, Klf2, Klf4 and Klf5 or a nucleic acid that encodes the same.

8. The agent according to claim 7, wherein the nuclear reprogramming substances further comprise:
(iv) a member of the Myc family selected from the group consisting of c-Myc, L-Myc and N-Myc or a nucleic acid that encodes the same.

9. The agent according to claim 7, wherein the nuclear reprogramming substances comprise Oct3/4, Sox2 and Klf4, or nucleic acids that encode the same.

10. The agent according to claim 8, wherein the nuclear reprogramming substances comprise Oct3/4, Sox2, Klf4 and c-Myc, or nucleic acids that encode the same.

11. The agent according to claim 8, wherein the nuclear reprogramming substances comprise Oct3/4, Sox2, Klf4 and L-Myc, or nucleic acids that encode the same.

12. The agent of claim 7, wherein the proteins belonging to cyclin D family are cyclin D1, cyclin D2 and cyclin D3.

13. The agent of claim 7, wherein the proteins belonging to cyclin D family are T286A cyclin D1 and cyclin D3.

14. The method of claim 1, wherein the cyclin D family member is selected from the group consisting of T286A cyclin D1 and cyclin D3.

15. A method of improving the efficiency of establishment of a reprogrammed mammalian cell, comprising
introducing into a mammalian somatic cell (a) expression vector(s) comprising nucleic acids that encode nuclear reprogramming substances and (b) an expression vector comprising a nucleic acid that encodes a cyclin D family member, and
culturing the mammalian somatic cell to form a colony of reprogrammed cells exhibiting morphological characteristics similar to an ES cell,
thereby improving the efficiency of establishment of the reprogrammed mammalian cell compared to the efficiency produced by the same method except that the introduction of the expression vector of (b) is not performed,
wherein the nuclear reprogramming substances comprise:
(i) Oct3/4,
(ii) a member of the Sox family selected from the group consisting of Sox1, Sox2, Sox3, Sox15, and Sox17, and
(iii) a member of the Klf family selected from the group consisting of Klf1, Klf2, Klf4 and Klf5.

16. The method of claim 15, wherein the mammalian cell is a mouse cell and the nuclear reprogramming substances comprise Oct3/4, Sox2 and Klf4.

17. The method of claim 15, wherein the mammalian cell is a human cell and the nuclear reprogramming substances comprise Oct3/4, Sox2, Klf4 and c-Myc.

18. The method of claim 15, wherein the cyclin D family member is selected from the group consisting of cyclin D1, cyclin D2, and cyclin D3.

19. The method of claim 15, wherein the cyclin D family member is selected from T286A cyclin D1 and cyclin D3.

* * * * *